United States Patent [19]

Bickel

[11] 4,129,041
[45] Dec. 12, 1978

[54] METHOD AND APPARATUS FOR RECEIVING ULTRASONIC WAVES BY OPTICAL MEANS

[75] Inventor: Wolf Bickel, Bergisch-Gladbach, Fed. Rep. of Germany

[73] Assignee: Krautkramer-Branson, Incorporated, Stratford, Conn.

[21] Appl. No.: 844,459

[22] Filed: Oct. 21, 1977

[30] Foreign Application Priority Data

Nov. 3, 1977 [DE] Fed. Rep. of Germany ....... 2710638

[51] Int. Cl.$^2$ ............................................. G01H 9/00
[52] U.S. Cl. ......................................... 73/657; 356/5
[58] Field of Search ......................... 73/655, 657, 643; 356/5, 32, 109, 256

[56] References Cited

U.S. PATENT DOCUMENTS

| | | | |
|---|---|---|---|
| 3,355,934 | 12/1967 | Foster | 73/657 |
| 3,952,583 | 4/1976 | Rosati | 73/655 |
| 4,046,477 | 9/1977 | Kaule | 356/109 |

OTHER PUBLICATIONS

J. V. Foster, A Laser Device For Remote Vibration Measurement, IEEE Transactions on Aerospace and Electronic Systems, Mar. 1967, pp. 154–157.

Primary Examiner—Richard C. Queisser
Assistant Examiner—John P. Beauchamp
Attorney, Agent, or Firm—Ervin B. Steinberg; Philip J. Feig

[57] ABSTRACT

Ultrasonic waves present on the surface of a workpiece are received free of physical contact by an optical sensing arrangement which includes a frequency stabilized single mode laser which illuminates the vibrating surface portion. Reflected light from the illuminated portion, which light is frequency modulated by the Doppler effect of the ultrasonic wave, is collected by a lens and applied to a narrow band absorption light filter. The frequency of the laser and the filter is selected to cause the center frequency of the light to fall at a point along the steepest slope of the filter absorption curve. The change in light frequency causes a corresponding change in light intensity passing through the light filter and the filtered light, now amplitude modulated, is provided to photoelectric means. A feedback circuit maintains the frequency of the laser constant.

16 Claims, 3 Drawing Figures

METHOD AND APPARATUS FOR RECEIVING ULTRASONIC WAVES BY OPTICAL MEANS

FIELD OF THE INVENTION

This invention concerns an ultrasonic test method and apparatus for receiving ultrasonic waves from a workpiece by optical means and, therefore, free of physical contact with the workpiece. More specifically, this invention concerns the sensing of an acoustic wave responsive surface deformation on a workpiece by means of a frequency stabilized single-mode laser, the light beam of which illuminates the workpiece area undergoing such deformation in synchronism with the frequency of the acoustic wave.

BACKGROUND OF THE INVENTION

For receiving ultrasonic energy free of physical contact with a workpiece, as is desired for certain nondestructive test applications, optical arrangements are preferred. Several types of interferometers can be used, but particularly suited for this type of application is a transit time interferometer disclosed in U.S. Pat. No. 4,046,477, dated Sept. 6, 1977 of W. Kaule entitled "Interferometric Method and Apparatus For Sensing Surface Deformation of a Workpiece Subjected to Acoustic Energy". Other known optical receiving arrangements are shown in "Werkstoffprufung mit Ultraschall" (book), J. & H. Krautkramer, 3rd edition, Springer Verlag, Berlin/Heidelberg/New York (1975) pp. 162 et seq.

BRIEF SUMMARY OF THE INVENTION

The present invention is based on the principle that the effect manifest upon a light beam which is incident upon a workpiece surface subjected to an acoustic wave is measured by optical means. Such a workpiece surface, responsive to an acoustic wave transmitted into the workpiece by known means and possibly reflected at a defect, vibrates as determined by the intensity of the sound wave and the elastic characteristics of the workpiece. The mechanical vibrations of the surface elements so affected about their steady state position will be identified as deformation of the surface or surface portion.

Recent arrangements utilize in general a laser providing a beam of coherent light which illuminates the workpiece surface.

The arrangements described above have the disadvantage that a spatial coherence of the light waves is necessary. Consequently, only the parallel part of the diffused light reflected by the receiving surface can be used. Receiving surface, as used herein, is that portion of the workpiece surface from which acoustic energy is to be received. Spatial coherence, as used herein shall denote a constant phase angle difference of the superposed light waves for each location of the light beam cross section. The light incident upon the workpiece surface undergoing deformation responsive to acoustic energy is subjected to diffused reflection. Hence, it is necessary to filter out parallel light which is accompanied by a significant loss of light intensity.

The problem pointed out above is overcome in the present invention by an arrangement in which the light reflected at the workpiece surface portion and frequency modulated by the Doppler effect, on account of the acoustic wave, is passed through a filter. The frequency of the laser is predetermined in such a manner that additional amplitude modulation of the reflected light occurs at the slope of the light filter absorption curve followed by demodulation using known methods to derive ultimately an electrical signal which is a function of the intensity of the ultrasonic energy and such signal being suitable for measurement or further evaluation.

If intense monochromatic light provided by a frequency stabilized single mode laser is used to illuminate the surface portion of a workpiece which undergoes deformation in synchronism with the frequency of the ultrasonic wave, the frequency of the diffused light is subjected to a shift in accordance with the Doppler principle. The diffused light, therefore, becomes frequency modulated in accordance with the frequency of the ultrasonic wave. For signal evaluation, e.g. to derive an electrical signal which is dependent upon the intensity of the ultrasonic wave, the frequency modulated light beam must be transformed into an amplitude modulated light beam which then is converted to an electrical signal by known photoelectric means. Direct demodulation of the frequency modulated light at the frequencies encountered ($10^{14}$ Hz) is technically not possible.

In accordance with this invention, amplitude demodulation of the light signal is achieved by operating along one slope of the light absorption curve of a filter. Such a filter, preferably, has a very steep slope associated with its light absorption (blocking) characteristic.

Further objects and characteristics of this invention will be more clearly apparent from the following description when taken in conjunction with the accompanying drawings:

DETAILED DESCRIPTION OF THE INVENTION

Figure 1:
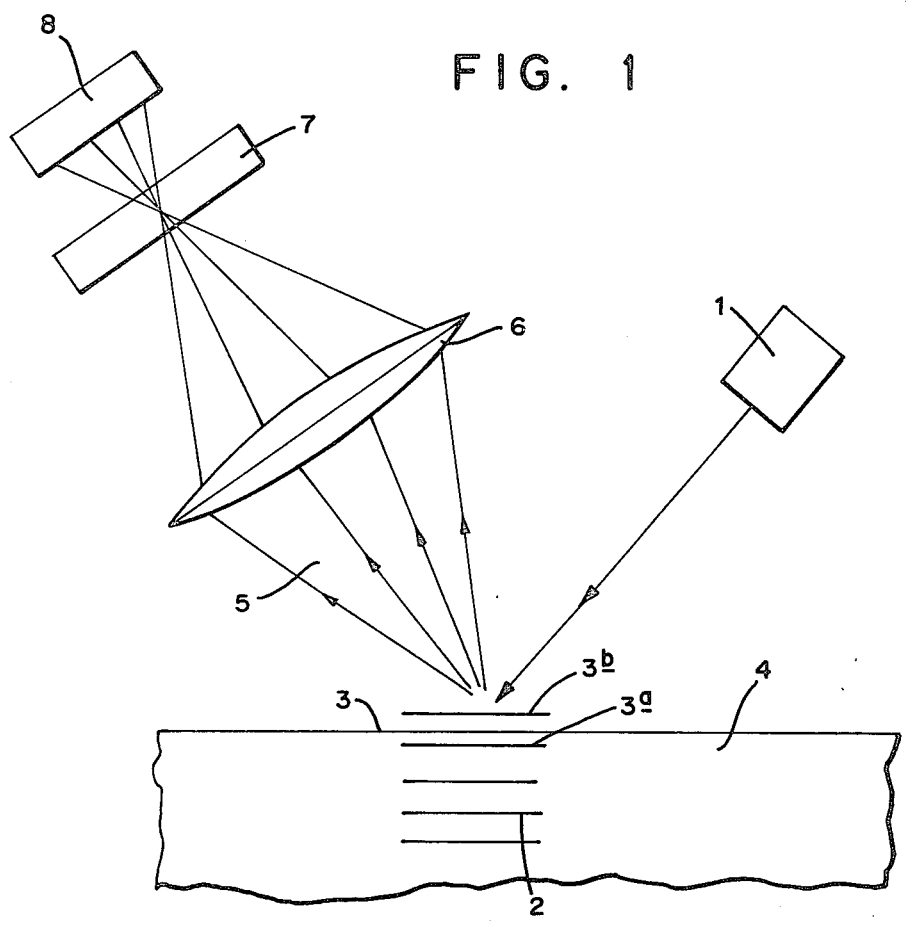
FIG. 1 is a schematic diagram of the optical arrangement required for the present invention.
Figure 3:
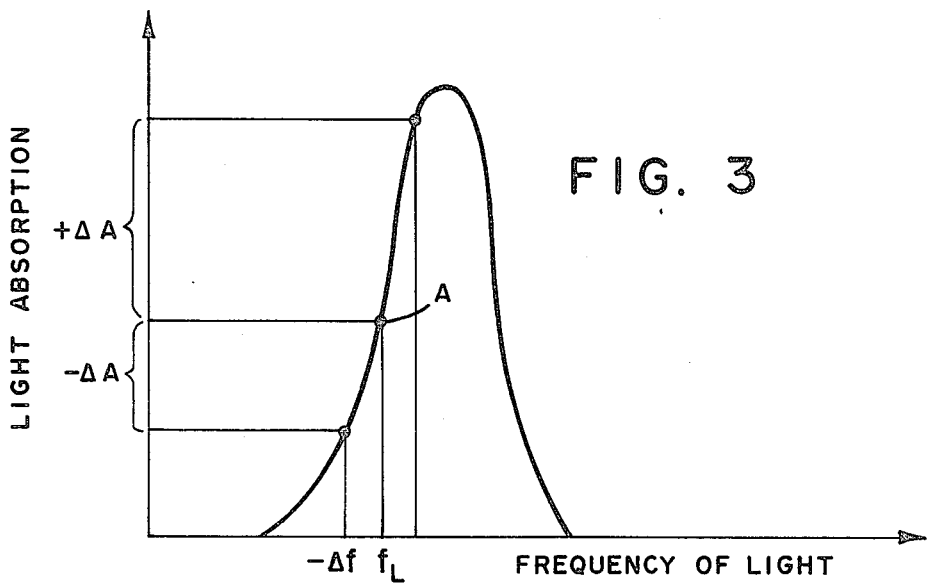
FIG. 3 is a graph of the frequency dependent blocking characteristic of a preferred light filter.
Figure 2:
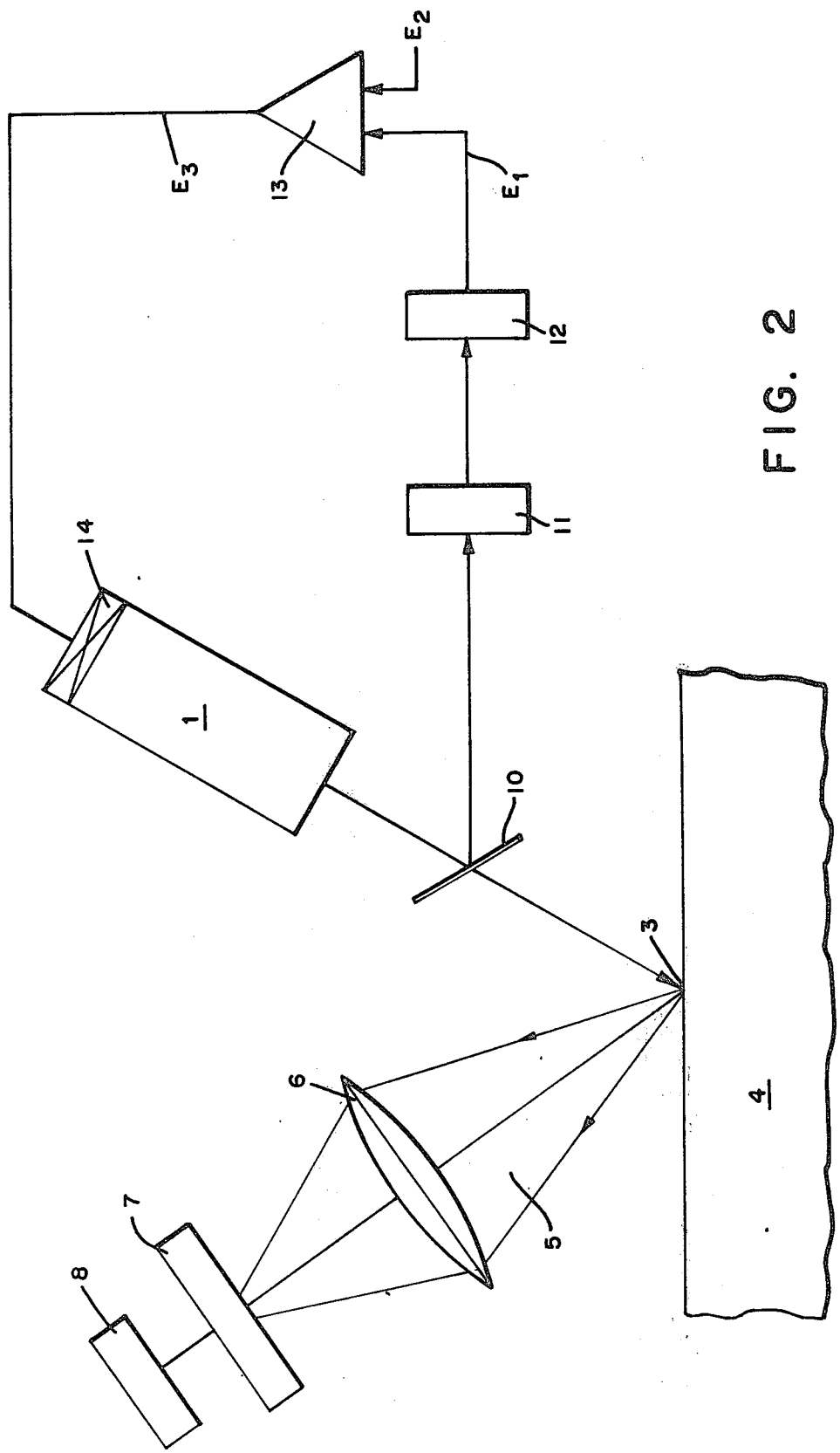
FIG. 2 is a schematic diagram, partly in block form, illustrating a circuit for providing frequency stabilization of the laser used.

With reference to FIG. 1, laser 1, a frequency stabilized single mode laser, transmits a beam of coherent light upon the surface portion 3 of a workpiece 4 which responsive to an acoustic wave 2 is cyclically deformed between the amplitudes 3a and 3b, shown in an exaggerated scale for the sake of clarity. The acoustic velocity, that is the speed at which the workpiece surface 3 portion vibrates, causes frequency modulation of the laser light in accordance with the known Doppler effect. Therefore, the diffused reflected light 5 contains the light frequencies $f_L - \Delta f$ to $f_L + \Delta f$ wherein $f_L$ is the frequency of the laser light and $\Delta f$ the frequency changes due to the Doppler effect upward and downward along the frequency scale. The diffused light 5 is brought to a convergence by a condensing lens 6 and the light collected from the surface portion 3 is then transmitted to a light filter 7. The absorption line, that is the blocking characteristic of the light filter, must be located in such a manner that the frequency of the laser light is disposed along the steepest slope portion of the filter, as seen in FIG. 3. Corresponding to the higher and lower values of $\Delta f$ the slope of the light filter provides an amplitude modulation $\Delta A$. Therefore, the light m the light filter 7 is frequency modulated as well as plitude modulated. The succeeding photodetector 8 iduces a modulated electrical output signal which is ponsive to the amplitude modulation of the light.

t is important that the laser is frequency stabilized so it the frequency is always located along the steepest tion of the slope of the absorption curve of the light er, a feature particularly critical for filters having y steep absorption curve slopes. Such a filter can be istructed by utilizing the absorption line of a suitable stance, see "Single Frequency Operation of Ion iers", M. W. Dowley, "Coherent Radiation", 1971, . 106 and "Wellenanlgenstabilisierung der grunen Ar — Laserlinie mit Hilfe gesattigter Absorption in einer rnen $^{129}I_2$ — Zelle", F. Spieweck, Metrologia, Vol. 15 (1976), pp. 43 to 46.

is is known, gasses under low pressure (in the order ne millibar) have very narrow absorption lines. For example given above using an argon-ion laser having its emission at 514 nm, a suitable filter comprises a isparent enclosure filled with iodine isotope $^{129}I_2$. s substance has sufficiently narrow and steep absorp- lines in the resonating range of the laser. By means piezoelectric control elements the resonator of the gle mode laser 1 is tuned in such a manner as to cause requency of operation to correspond to the desired nt along the iodine absorption line, see point A of i. 3.

his requirement can be met by the provision of a lback circuit shown in FIG. 2. The laser resonator 1 vides a beam of light for illuminating the surface 3. mall portion of the light is reflected at the transpar- mirror 10 and passed through an absorption filter 11 photoelectric detector 12. The absorption filter 11 responds exactly to the filter 7 of FIG. 1 and com- es $^{129}I_2$ vapor. The photoelectric detector 12 pro- s to the differential amplifier 13 a voltage signal $E_1$ ch is proportional to the laser light passed through filter 11. The amplifier also receives as an input a age $E_2$ adjusted for a predetermined value. The trical output signal $E_3$ from the amplifier 13, which al is proportional to the difference between both it voltages, controls a piezoelectric element 14 for isting the length of the laser resonator 1. Each nge of frequency of the laser, operating at constant litude output, produces a change of light amplitude aused by the absorption filter 11. Hence, there will ur a corresponding change in the output voltage at photoelectric detector 12, which voltage is com- d with the predetermined value at the input to lifier 13. Any difference signal is amplified and lied to the piezoelectric control element 14 which ists the length of the resonator in such a manner as orrect the frequency deviation.

he predetermined voltage value at the input of the rential amplifier 13 determines the point of opera- along the slope of the iodine absorption filter line. e the absorption filter 11 corresponds exactly with filter 7, the point of operation at the filter 7 is main- ed constant. FIG. 3 clearly illustrates obtaining litude modulation along the slope of the curve of absorption filter chracteristic. The absorption line of $^{129}I_2$ filter used in the described arrangement typi- y has the characteristic curve corresponding to i. 3 which depicts the light absorption properties of filter as a function of light frequency. The frequency f the laser is given by the point of operation A and abilized thereat as a result of the predetermined voltage value fed to the input of the differential amplifier 13, see FIG. 2.

The frequency $f_L$ changes corresponding to the ultrasonic sound wave as the result of the Doppler effect by the value $\pm \Delta f$. Such a change causes along the slope of the iodine line an amplitude modulation change $\pm \Delta A$ of the light passed through the filter 7. For the higher light frequency $f_L + \Delta f$ highest light absorption occurs, and for $f_L - \Delta f$ lowest light absorption results. The amplitude modulated light is transformed into an electrical signal by photoelectric means 8, FIGS. 1 and 2, which signal can be processed further. The change in output of the electrical signal from the photoelectric means is responsive to a frequency change of the laser light and, hence, is a measure of the velocity amplitude of the ultrasonic wave present at the workpiece surface.

While in the description heretofore, the operating point $f_L$ is located at the ascending slope of the absorption curve, it should be understood that the point $f_L$ could be located also along the descending slope of the curve, the only change being then a phase reversal of the electrical output signal.

In an alternative embodiment of the present invention, instead of utilizing the absorption line of gasses, a suitably stained light filter as normally used in optics may be used. A filter of this type will have only a single slope. Alternatively, an interferometer arrangement of the Fabry - Perot type can be employed, see "Principles of Optics" (book), Max Born et al, 4th edition 1970, Pergamon Press.

Another absorption medium comprises the isotope $^{127}I_2$ in combination with an argon-ion laser used at 514 nanometer wavelength. A further light filter suitable for the present invention includes an interference filter assembly which comprises several thin filter layers applied to a transparent support plate. Such assemblies are commercially available products and made, for instance, by Jenaer Glaswerk Schott & Gen., Mainz, West Germany.

Finally lens 6 may be replaced, in an alternative embodiment, by a set of mirrors or if desired, mirrors in combination with a lens.

The present invention is characterized by the advantage that by means of a powerful condensing lens, or lens combination, a large part of the diffused light is collected and, hence, used for measurement obviating, therefore, the need to consider spatial coherence effects.

What is claimed is:

1. The method for receiving an ultrasonic wave from a workpiece surface portion by optical means free of physical contact with such workpiece portion comprising:
   transmitting a beam of light from a frequency stabilized single mode laser upon the workpiece surface portion which undergoes deformation responsive to the presence of an ultrasonic wave, thereby causing frequency modulation of the incident light;
   collecting the diffused frequency modulated light reflected at said surface portion and transmitting said light through a light filter having at least one steep light absorption line, whereby the frequency of said laser and that of the light filter is selected to cause the nominal frequency of said laser to be disposed along the steep part of the slope of the light absorption line of the filter to thereby provide amplitude modulated light passed through the filter, and transmitting the amplitude modulated light to photoelectric sensing means adapted to provide an electrical output signal which is responsive to the amplitude modulated light passed through the filter.

2. The method for receiving an ultrasonic wave from a workpiece surface portion as set forth in claim 1, said light filter being a gaseous medium.

3. The method for receiving an ultrasonic wave from a workpiece surface portion as set forth in claim 1, said light filter being an absorption filter.

4. The method for receiving an ultrasonic wave from a workpiece surface portion as set forth in claim 1, said light filter being a Fabry - Perot interferometer.

5. The method for receiving an ultrasonic wave from a workpiece surface portion as set forth in claim 1, said light filter being a narrow band absorption filter.

6. An apparatus for receiving an ultrasonic wave from a workpiece surface portion by optical means free of physical contact with such workpiece portion comprising:
a frequency stabilized single mode laser disposed for transmitting a beam of coherent light upon the workpiece surface portion undergoing deformation responsive to the presence of an ultrasonic wave which causes the light to become frequency modulated;
a light filter;
means disposed for receiving the diffused frequency modulated light reflected at said surface portion and transmitting the reflected light through said light filter, the frequency of said laser and that of said filter being selected to cause the nominal frequency of said laser to be disposed along the steep portion of the slope of the light absorption line of said filter, whereby to provide amplitude modulated light passed through said filter, and
photoelectric means disposed for receiving the amplitude modulated light passed through said filter and providing an electrical output signal responsive to the light transmitted through said filter.

7. An apparatus for receiving an ultrasonic wave as set forth in claim 6, said filter being a gaseous medium.

8. An apparatus for receiving an ultrasonic wave as set forth in claim 6, said filter being an absorption filter.

9. An apparatus for receiving an ultrasonic wave as set forth in claim 6, said filter being a narrow band absorption filter.

10. An apparatus for receiving an ultrasonic wave as set forth in claim 6, said filter being of the Fabry - Perot interferometer type.

11. An apparatus for receiving an ultrasonic wave as set forth in claim 6, said means disposed for receiving including an optical condensing lens.

12. An apparatus for receiving an ultrasonic wave as set forth in claim 6, said filter comprising an interference filter.

13. An apparatus for receiving an ultrasonic wave as set forth in claim 6, said means disposed for receiving including mirror means.

14. An apparatus for receiving an ultrasonic wave as set forth in claim 6, and a control circuit coupled for using a portion of the light transmitted from said laser as a feedback signal to maintain the frequency of said laser at its predetermined frequency.

15. An apparatus for receiving an ultrasonic wave as set forth in claim 14, said control circuit including an optical reflecting surface for receiving a portion of the light transmitted, a further filter disposed to cause said light portion to be transmitted thereto, a photoelectric means for providing an electrical signal responsive to the light passed through the further filter, a differential amplifier for receiving said electrical signal from said photoelectric means and comparing it with a predetermined signal and providing a corresponding further electrical output signal, and a piezoelectric element coupled to the resonator of said laser for receiving said further electrical output signal and adjusting the length of said resonator, whereby to control the frequency of said laser.

16. An apparatus for receiving an ultrasonic wave as set forth in claim 15, said filter and said further filter have substantially the same absorption characteristics.

* * * * *